United States Patent [19]

Jaeger et al.

[11] Patent Number: 5,221,653
[45] Date of Patent: Jun. 22, 1993

[54] PREPARATION OF BI/FE MOLYBDATE COATED CATALYSTS DOPED WITH PHOSPHORUS AND POTASSIUM

[75] Inventors: Philippe Jaeger, Salindres; Olivier Legendre, Herblay, both of France

[73] Assignee: Rhone-Poulenc Chimie, Courbevoie, France

[21] Appl. No.: 811,127

[22] Filed: Dec. 20, 1991

[30] Foreign Application Priority Data

Dec. 20, 1990 [FR] France ............... 90/16389

[51] Int. Cl.⁵ ............... B01J 27/185; B01J 27/192; B01J 23/78; B01J 37/28
[52] U.S. Cl. ............... 502/212
[58] Field of Search ............... 502/212

[56] References Cited

U.S. PATENT DOCUMENTS

| | | | |
|---|---|---|---|
| 4,077,912 | 3/1978 | Dolhyj et al. | 502/178 |
| 4,148,757 | 4/1979 | Brazdil et al. | 502/212 X |
| 4,166,808 | 9/1979 | Daumas et al. | 502/249 |
| 4,267,386 | 5/1981 | Vanderspurt | 568/479 X |
| 4,298,763 | 11/1981 | Engelbach et al. | 568/479 |
| 4,414,134 | 11/1983 | Friedrich et al. | 502/204 |
| 4,438,217 | 3/1984 | Takata et al. | 502/212 X |
| 4,537,874 | 8/1985 | Sato et al. | 502/212 X |
| 4,541,964 | 9/1985 | Katsumata et al. | 502/212 X |
| 4,710,484 | 12/1987 | Dolhyj et al. | 502/212 X |
| 5,017,542 | 5/1991 | Martan et al. | 502/212 X |
| 5,082,819 | 1/1992 | Boeck et al. | 502/212 |

*Primary Examiner*—W. J. Shine
*Assistant Examiner*—Douglas J. McGinty
*Attorney, Agent, or Firm*—Burns, Doane, Swecker & Mathis

[57] ABSTRACT

Coated catalyst particulates, well adopted for the oxidation of olefins into $\alpha,\beta$-unsaturated aldehydes, e.g., for the oxidation of propylene into acrolein, and the coating layer of which comprising a catalytically active phase including a catalytically effective amount of bismuth and iron molybdate and dopant amounts of phosphorus and potassium, are prepared by providing a calcined and ground catalytically active intermediate composition devoid of phosphorus and potassium values, coating this intermediate composition onto a particulate support substrate comprising rough-surfaced inert and solid spheres, also coating phosphorus and potassium values onto the particulate support substrate, and then calcining the support particulates thus coated.

20 Claims, No Drawings

PREPARATION OF BI/FE MOLYBDATE COATED CATALYSTS DOPED WITH PHOSPHORUS AND POTASSIUM

CROSS-REFERENCE TO COMPANION APPLICATION

Copending application Ser. No. 07/811,128, filed concurrently herewith and assigned to the assignee hereof, now allowed.

BACKGROUND OF THE INVENTION

1. Field of the Invention

The present invention relates to the preparation of coated catalysts based on the molybdates of bismuth and iron and doped with phosphorus and potassium values.

This invention especially relates to the preparation of such coated catalysts via the production of a catalytically active intermediate composition, next calcining and grinding this intermediate and then coating particles of a solid and inert support substrate, the external surface of which is rough, with said ground composition or a mixture comprised thereof, followed by the calcination of the particulates thus coated.

2. Description of the Prior Art

French Patent No. 2,047,199, equivalent to U.S. Pat. No. 3,959,384, describes oxidation catalysts corresponding to the general formula:

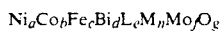

$Ni_aCo_bFe_cBi_dL_eM_nMo_fO_g$ in which
L is particularly phosphorus,
M is particularly potassium,
a and b are numbers ranging from 0 to 15 and the sum (a+b) ranges from 2 to 15,
c is a number ranging from 0.5 to 7,
d is a number ranging from 0.1 to 4,
e is a number ranging from 0 to 4,
f has a value of 12,
g is a number ranging from 35 to 85, and
n is a number ranging from 0.01 to 0.5

These catalysts are prepared by formulating a suspension in aqueous medium from various precursors of the elementary constituents of the catalyst, by adding a support (such as a silica gel) to said suspension which is essentially a paste, and by heating this to dryness to provide a cake which is then treated at elevated temperature in the presence of air.

The catalysts are employed in the form of particles or of tablets.

These catalysts, both in bulk form and diluted, are effective, but they present difficulties over the course of an oxidation process on an industrial scale. Indeed, in a fixed bed, locally elevated temperatures may arise to initiate an undesirable violence of the reaction.

French Patent No. 2,202,729, equivalent to U.S. Pat. No. 4,077,912, describes that it is advantageous to employ catalysts for the oxidation of propylene to acrolein which are prepared by coating, namely, formed of a catalytically active layer of analogous composition, but deposited onto the external surface of an inert support of at least 20 microns in diameter, instead of diluting it with a support introduced with the metallic salts. It is then possible to better control the evolution of the heat of reaction in fixed beds processes.

Nevertheless, this particular technique for producing the catalyst requires a significant portion thereof to be constituted by the inert support (66% by weight of the finished catalyst, according to the sole example of this '729 patent). The fraction reserved for the active phase in comparison with the former simply diluted catalysts is decreased, which results in a very disadvantageous decrease in the activity of the catalysts.

This may manifest itself industrially in the obligation either to use larger reactors to preserve the production capacity and identical operating conditions, or to increase the reaction temperature to preserve the production capacity and the size of the reactor. In the first instance, the major disadvantage is economic. In the second instance, two disadvantages are presented: the selectivity for acrolein will diminish and the activity of the catalyst will decrease more rapidly over the course of time.

U.S. Pat. No. 4,298,763 describes, for the oxidation of propylene into acrolein, a calcined catalytic composition (active phase) corresponding to the general formula:

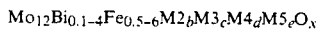

$Mo_{12}Bi_{0.1-4}Fe_{0.5-6}M2_bM3_cM4_dM5_eO_x$ in which M2 is nickel and/or cobalt, b is a number ranging from 2 to 12, M3 is particularly K, c is a number ranging from 0.01 to 0.1 and preferably from 0.03 to 0.09, M4 is P, d is a number ranging from 0 to 1 and preferably from 0.01 to 0.02, M5 is In and/or Na, e is a number ranging from 0 to 0.5 and preferably from 0.01 to 0.02, and x is the number of atoms of oxygen required to satisfy the valencies of the other constituents.

This active phase is deposited as a layer of thickness 150 to 1500 $\mu$m and of surface area less than 15 m$^2$/g.

The deposition of the layer of calcined and pulverulent catalytic material, the dimension of the particles ranging from 0.1 to 300 $\mu$m, is carried out in moist medium, the support particles being vigorously stirred and controlled operating conditions moreover being required.

The layer coating the central supporting core constituted at least 50% of the weight of the support, namely, at least 33% by weight of the finished catalyst and at most 250% of the weight of the support, namely, at most 71.4% by weight of the finished catalyst.

Prior to being used for the oxidation of olefins, the coated catalyst is dried and, if necessary, calcined at a temperature of 400° to 700° C.

It will be seen from this '763 patent that the totality of the constituents of the catalytic composition coating the particular support is present prior to the calcination and the grinding of such composition.

Example 1 of the patent describes a composition containing 0.06 atoms of phosphorus and 0.06 atoms of potassium per 12 atoms of molybdenum, the former two elements being introduced into the aqueous solutions in the form of KOH and phosphoric acid before precipitation, and also atomization of the entirety of the suspension. The atomized precursor is then remixed with another aqueous potash solution before extrusion and then drying and calcination.

The dopants are therefore introduced into the precursor of the active phase before such active phase forms during calcination. This technique for the introduction of the dopants values presents the following major disadvantages:

(1) a greater complexity because it is necessary to introduce the potash in two different operations, which necessitates two weighings and therefore gives rise to two risks of error;

(2) a significant loss of phosphorus dopants within the particles of precursors, even though the desirable function of the dopants is exerted on the surface of the particles of the active phase, whereat the catalytic reactions occur;

(3) a poor control of the microscopic distribution of the potassium added after the atomization, by mixing. Such a precursor, merely dried by atomization, generally includes sites of absorption of cations of sufficient strength to obstruct the homogeneous distribution of all of the potassium on all of the particles of solids. A poor control of the atomic ratio of phosphorus to potassium on the particle scale results, an atomic ratio whose value significantly affects the activity of the finished catalyst.

U.S. Pat. No. 4,621,072 particularly relates to a process for the preparation of coated catalysts which are resistant to abrasion, comprising an inert support having a rough surface and particle dimensions of 0.5 to 6 mm and a layer of catalytically active material coated onto the support and fixed thereto.

This '072 patent describes in detail the difficulties encountered in the preparation of coated catalysts in order to obtain a coating layer having mechanical properties sufficient that the catalysts can be used on an industrial scale in fixed bed reactors. The patent also proposes various measures to overcome these disadvantages and recommends, inter alia, using a suspension of a precursor of the catalytically active material also containing a binder and, if necessary, a porogenic agent. In this instance too, the precursor contains all of the constituents required for the production of a catalytically active material via a final specific thermal calcination treatment.

It will also be seen that particular care is required in the coating process to attain a good mechanical resistance despite a significant proportion by weight of active phase in the finished catalyst.

In this instance also the aforesaid technique for the introduction of the potassium and/or phosphorus dopants presents the above disadvantages.

In addition, in this process, as in all of those discussed above, the suitable soluble salts used in the preparation of the catalytically active phase are the metallic nitrates, ammonium molybdate, potassium nitrate and phosphoric acid. Ammonium nitrate will therefore be formed during this preparation and will decompose thermally at approximately 230° C. during the subsequent calcination.

It is apparent that this thermal decomposition of ammonium nitrate poses serious practical problems. Indeed, one skilled in this art is well cognizant that ammonium nitrate is an explosive compound and, in this respect, is dangerous to handle at the industrial level.

French Patent No. 2,481,146, equivalent to U.S. Pat. No. 4,382,880, moreover describes a process for the preparation of catalysts based on the oxides of molybdenum and/or tungsten and the oxides of other metals. This process permits the thermal decomposition of ammonium nitrate to be avoided. It is characterized in that, in a first stage, to a first aqueous solution containing the ammonium, molybdenum and tungsten salts, a second solution containing the metallic salts is added. In a second stage, ammonia is added to the mixture obtained until a pH greater than the pH of the beginning first aqueous solution is filtered to provide the cake which will then be calcined to produce the active phase.

This procedure enables the ammonium nitrate, which is soluble in the mother liquors, to be easily separated, on the one hand, and the precursor of the active phase, in the form of a filter cake, on the other. It is applicable to formulations based on molybdates of bismuth and of iron described in the above patents with the exception that, since one skilled in this art is well aware that potassium nitrate and phosphoric acid are soluble under the conditions employed, these elements will be entrained in the mother liquors. It is therefore not possible in this manner to introduce a specific amount of phosphorus and of potassium into the active phase in a controlled manner.

SUMMARY OF THE INVENTION

Accordingly, a major object of the present invention is the provision of an improved process for the preparation of coated catalytic compositions based particularly on the molybdates of bismuth and of iron and, if necessary, other elements, containing phosphorus and potassium dopants, which improved process avoids the above risks, is relatively simple to carry out and provides a suitable distribution of the dopants in the catalytically active layer, a precise control over the final catalytic composition and ensures a satisfactory degree of reproducibility. The final product coated catalysts have satisfactory mechanical resistance and the dopants therein, phosphorus and potassium, are present in the least possible amounts.

Briefly, the present invention features a process for the preparation of coated catalysts of the molybdates of bismuth and of iron, doped notably with phosphorus and potassium, comprising producing a catalytically active intermediate composition, calcining and grinding said intermediate composition, next coating particles of a solid and inert support substrate whose external surface area is rough with said ground composition or mixture comprised thereof, and then calcining the particles thus coated, and wherein:

(a) the catalytically active intermediate composition is devoid of potassium and of phosphorus, and (b) the potassium and phosphorus values are introduced into the catalysts during the coating stage.

DETAILED DESCRIPTION OF THE PREFERRED EMBODIMENTS OF THE INVENTION

More particularly according to the present invention, a catalytically active intermediate composition devoid of potassium and phosphorus values is first prepared.

The precise nature of such intermediate composition (undoped or intermediate active phase) is not critical, since it contains the chemical elements conventionally used for the production of high-performance catalysts for the oxidation of propylene to acrolein. It is essentially constituted of bismuth molybdate and of iron and can be represented by the following formula:

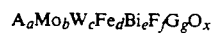

in which A is at least one metal selected from among cobalt, nickel, manganese, zinc, magnesium, lead, chromium, vanadium, cerium and lanthanum; F is at least one element selected from among arsenic, indium, antimony, tin, tellurium, selenium, silicon, sulfur and boron; G is at least one element selected from among the alkaline earth metals, niobium and thallium; a is the sum of the indices ascribed to each of the metals A and ranges from 0 to 12; b and c are numbers each ranging from 0 to 12, their sum being equal to 12; d is a number ranging from 0.2 to 6, preferably from 0.5 to 3; e is a number ranging from 0.2 to 6, preferably from 0.5 to 3; f is the sum of the indices ascribed to each of the elements F and ranges from 0 to 4, preferably from 0.5 to 2; and g is the sum of the indices ascribed to each of the elements G and ranges from 0 to 4, preferably from 0.5 to 2.

This intermediate composition (undoped catalytic phase) is prepared according to methods per se known to this art, particularly by the precipitation techniques described in French Patents Nos. 2,481,146 and 2,491,778, which are equivalent to U.S. Pat. Nos. 4,382,880 and 4,418,007, respectively. The method described in the '146 patent can be summarized as follows:

In a first stage, a solution of the soluble salts, nitrates or chlorides, of the metals of group A and of iron and of bismuth are prepared in a first aqueous solution, acidified by nitric acid to avoid hydrolysis of bismuth. The pH of this first solution ranges from 1 to 2. In a second stage, this first solution is introduced into a solution of ammonium heptamolybdate and optionally of ammonium paratungstate and of soluble compounds of the elements F and G, with vigorous stirring. A first precipitation occurs. In a third stage, ammonia is added, still with stirring, until the pH is increased to between about 6 and about 9 and the precipitation is thus completed. It is possible to add the dopants F and G at this time, in the form of insoluble compounds.

The ammonia solution contains between 50 and about 250 g of ammonia and it is added at a rate ranging from about 20 to about 200 g of ammonia per hour and per liter of mixture. It is preferable to heat the suspension thereafter to from 30° to 100° C. for about one hour to complete the precipitation of the specie. The suspension is then filtered.

The filter cake is then spread to a thickness of less than 6 cm, then placed in ovens. Calcination is carried out by increasing the temperature progressively at a rate of 100° to 200° C. per hour. The temperature is then maintained at a stable value between 400° and 460° C for 6 hours, and then cooling is carried out over the course of a few hours.

The intermediate composition proposed in this manner is then ground by known means in order that its particle size does not exceed 400 micrometers.

The process according to the present invention comprises the coating of particles of a solid support.

Useful supports for the process according to the invention comprises solid spheres of a diameter ranging from 0.5 to 6 mm, a precise value of which is easily determined by one skilled in this art as a function of the loss of charge introduced into the oxidation reactor. The chemical nature of this support is not critical, provided that it is chemically inert with respect to the reagents. Silica, alumina, silica-alumina, sintered clay, carborundum, magnesia or magnesium silicate are advantageously thus employed.

It is desirable that the support have a surface roughness which can be defined by the height of the unevennesses (protuberances) relative to the average diameter of the sphere. This ratio preferably ranges from 0.1 to 0.2.

The coating is the operation by which support spheres are progressively enveloped within an external layer of active phase. This operation is carried out in a manner known per se by introduction of said spheres into a revolving coater equipped with means for introducing particles of ground active phase as indicated above and with means for introducing an aqueous solution of adhesive agent. According to an essential characteristic of the process of the invention, the introduction of potassium and of phosphorus is carried out during the coating stage.

In one embodiment of the invention, at least one compound of potassium and at least one compound of phosphorus is introduced into the coater in the form of finely ground powder, simultaneously with the intermediate catalytic composition and a solution of an adhesive agent.

In another embodiment of the invention, this introduction is carried out in the coater by introduction of an aqueous solution of at least one potassium compound and at least one phosphorus compound. Preferably, the solubility in water of the phosphorus compound(s) and of the potassium compound(s), measured at 25° C., is greater than 10 g/l.

The potassium and phosphorus compounds are selected from among those which are inert with respect to the other components of the coating solution, particularly the adhesive agent and, if applicable, the porogen. These compounds should, in addition, be capable of being decomposed by heat during the subsequent calcination and should not destroy the adhesive agents and the porogens. In actual practice, the addition of the selected phosphorus and potassium compounds should adjust the aqueous solution to a pH value ranging from 3 to 11.

Potash is a suitable compound of potassium; inorganic or organic phosphates and phosphoric acid are examples of suitable compounds of phosphorus.

In a preferred embodiment of the present invention, the two elements are introduced simultaneously by using a common compound such as potassium dihydrogen phosphate or potassium monohydrogen phosphate, it being possible to provide the remainder of each of the elements which may be necessary by addition either of potash or of phosphoric acid. The salts of heteroacids corresponding to the general formula $K_xH_{l-x}PMo_{12}O_{48}$ in which x ranges from 0 to 3 are also examples of suitable phosphorus compounds, if necessary, which are common to potassium.

In another preferred embodiment of the process according to the invention, the phosphorus and potassium compounds are introduced into the aqueous solution of adhesive agent.

The coating operation is conducted in a revolving coater operating at between 10 and 20 revolutions per minute in which 80 to 160 kg of rough support spheres from which dust has carefully been removed are placed. By means of a chute, between 30 and 50 kg/h of the ground intermediate catalytic composition and, by means of a pump under pressure, between 8 and 15 l/h of an aqueous solution of adhesive agent and of said phosphorus and potassium compound(s) are then simultaneously introduced. In a preferred embodiment, the spheres have previously been moistened with an aqueous solution of adhesive agent not containing dopant.

The operation is continued until all of the coating solution and then all of the intermediate active phase is utilized. The rotation is maintained for a few minutes to very effectively compress the layer of active phase on the spheres. They are then dried by hot air at a temperature of from 80° to 150° C. for 10 to 30 minutes and introduced into ovens. The temperature of these ovens is increased linearly over the course of 3 to 15 hours to a stable value between 450° and 500° C. Cooling then is carried out over the course of 3 to 10 hours. In a preferred embodiment, a second calcination is carried out successively and under the same conditions of variation of temperature as in the first calcination. In another preferred embodiment, the stable calcination temperature is 480° C.

The incorporation of the dopants is virtually total and reproducible: it is possible to introduce into the aqueous solution used during the coating only a close quantity (within 5%) to the quantity of phosphorus and potassium compound(s) theoretically required to provide the desired stoichiometry for the final catalytic composition.

In addition, the simplicity in carrying out the process according to the invention is quite remarkable. The quality of the incorporation constitutes a particularly notable advantage when coated and particularly active catalytic compositions are prepared of which the active phase (coating layer) constitutes from 15% to 33% by weight and corresponds to the general formula:

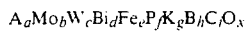
$$A_aMo_bW_cBi_dFe_eP_fK_gB_hC_iO_x$$

in which A is an atom of cobalt, nickel, manganese, magnesium and/or lead, and preferably of cobalt and/or of nickel; B is an atom of arsenic and/or of boron; C is an atom of an alkali metal other than potassium and/or an atom of an alkaline earth metal other than magnesium; a is the sum of the numbers of atoms of the elements A and ranges from 2 to 12, inclusive (when A is cobalt alone, a ranges from 8 to 10, inclusive); b is a number ranging from 10 to 12, inclusive; c is a number ranging from 0 to 2, inclusive, and the sum (b+c) has a value of 12; d is a number ranging from 0.5 to 4, inclusive; e is a number ranging from 0.5 to 4, inclusive; f and g are each numbers ranging from 0.005 to 0.06, inclusive, and, preferably, from 0.01 to 0.03, inclusive; h is the sum of the numbers of atoms of the elements B and ranges from 0 to 4, inclusive; i is the sum of the numbers of atoms of the elements C and ranges from 0 to 0.5, inclusive; and x is the number of atoms of oxygen required to satisfy the valencies of the other constituents.

Preferably, A is an atom of cobalt; the ratio f/g advantageously ranges from 0.3 to 3, inclusive, and, preferably, from 0.5 to 1.5, inclusive.

These catalytic compositions having a low amount of dopants P and K provide both a long-lived and high catalytic activity and selectivity during the preparation of acrolein by oxidation of propylene.

In order to further illustrate the present invention and the advantages thereof, the following specific examples are given, it being understood that same are intended only as illustrative and in nowise limitative.

EXAMPLE 1

(a) Preparation of the intermediate active phase 83.8 kg of ammonium heptamolybdate were dissolved in 380 liters of demineralized water, the resistivity of which being greater than 150,000 Ohm.cm, by heating to a temperature of from 70° to 80° C. The solution was then cooled to from 20° to 25° C. The pH was between 5 and 5.5.

In another reactor, 75 liters of the same demineralized water were introduced and heated to 80° C. 115.1 kg of cobalt nitrate hexahydrate, 16.5 kg of ferric nitrate hydrated with 9 molecules of water, 2.2 liters of 100% nitric acid and, finally, 19.2 kg of bismuth nitrate pentahydrate were then introduced, with stirring. After complete dissolution, the temperature was reduced to from 20° to 25° C.

The solution of the metallic nitrates was introduced over the course of 30 minutes into the solution of heptamolybdate with vigorous stirring and the pH decreased to between 1 and 1.5. 75 liters of a solution containing 200 grams of ammonia per liter were then added over the course of 30 minutes to the suspension obtained. The pH increased again to 7.

The temperature of the medium was adjusted over the course of one hour to 60° C. where it was maintained for 4 hours with stirring, then it was reduced over the course of 30 minutes to about 22° C.

The suspension was filtered, then washed with 500 liters of demineralized water of resistivity greater than 150,000 Ohm.cm. The cake was then deposited on plates having a thickness of approximately 4 to 5 cm. The plates were placed in an electric oven at 120° C. for 20 hours.

The oven was then heated over the course of 5 hours to a temperature of 400° C. which was maintained for 6 hours with circulation of air. Cooling to ambient temperature was carried out over the course of 5 hours.

The content of the plates was introduced into a pin mill to provide a particle size of less than 125 micrometers. About 102 kg of intermediate active phase were thus obtained.

(b) Coating was carried out in a coater of 1.25 m diameter revolving at between 15 and 18 revolutions per minute and containing at the beginning of the operation 125 kg of inert support spheres of clay sintered at high temperature, and from which any dust was carefully removed. The spheres were previously wetted by a first solution of glucose at 100 g per liter sprayed at a rate of 10 to 12 liters per hour.

When all of the spheres were wetted, a chute permitted 44 kg of intermediate active phase in powder form to be introduced over about 50 minutes. During the introduction of the powder, the coater continued to revolve and 12 liters of a second solution containing 100 g/l of glucose, but also 5 g/l of potassium dihydrogen phosphate, were sprayed onto the spheres. Once the entirety of the solution, then the entirety of the intermediate active phase had been introduced, the rotation was maintained for about a few minutes. Finally, a flexible connection permitted a supply of 1.3 to 15 m³ per hour of air heated to 100° C. to be directed onto the rotating spheres to dry them over the course of 15 to 20 minutes.

The spheres coated and dried in this manner were introduced into ventilated ovens to undergo a final calcination. The temperature of these ovens was progressively adjusted to 240° C. over the course of 6 hours, then to 480° C. over the course of 8 hours. A first stage of 6 hours at 480° C. was carried out, then a cooling to 150° C. over the course of 10 hours was followed by a heating over the course of 10 hours to 480° C. A second stage of 6 hours at 480° C. was followed by final cooling over the course of 10 hours to ambient temperature.

About 169 kg of finished catalyst were then removed from the oven, of which 26% constituted the active phase corresponding to the formula:

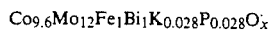
$$Co_{9.6}Mo_{12}Fe_1Bi_1K_{0.028}P_{0.028}O_x$$

COMPARATIVE EXAMPLE A 100 kg of calcined intermediate active phase, prepared following the operating conditions indicated in Example 1, were mixed in a mixer with 4 liters of an aqueous solution containing 270 g of potassium dihydrogen phosphate. The mixing proved difficult because it considerably decreased the viscosity of the preparation. After about 15 minutes, the entire mass was then dried for 15 hours at 120° C. in an oven.

44 kg of the active phase doped in this manner were then coated following the same protocol with the exception that potassium dihydrogen phosphate was not used in the second coating solution.

The drying and the calcination were identical to those described in Example 1.

COMPARATIVE EXAMPLE B

Another catalyst was prepared under conditions identical to those of Example 1, except that potassium dihydrogen phosphate was not introduced into the coating solution.

EXAMPLE 2

Incorporation and Distribution of the Dopants into the Layer of Active Phase In order to ascertain the degree of incorporation and the quality of the distribution of the dopants in the finished catalyst, it was necessary to determine the elements phosphorus and potassium in the thickness of the layer of active phase of the catalysts. Physical separation of different fractions of the layer of active phase by mechanical attrition was first carried out.

Thus, 30 g of finished catalyst were introduced into a closed metallic container of 50 ml capacity. The entire assembly was introduced into a apparatus which produced vertical oscillations of about 4 cm amplitude 700 times a minute.

At the end of 10 minutes, the apparatus was stopped and the container was opened. The spheres of catalyst were separated by sieving the active phase dust detached by attrition. This dust was collected, weighed and then dissolved to determine the dopants. The phosphorus was determined by plasma emission spectrometry and the potassium by flame emission spectrometry.

Next, the spheres were replaced in the container and the attrition was extended for an additional 10 minutes. A fresh fraction of active phase was collected and then determined. The operation was repeated twice more until there was virtually no more active phase visible on the catalysts subjected to attrition, which were virtually reduced to their central inert spheres.

From the mass of each collection, it was possible to estimate the position where the fraction of active phase collected was located, assuming that the attrition had occurred in a perfectly progressive manner, namely, the first collection only corresponded to the outermost particles and the last collection only to the innermost particles of the layer. This hypothesis, which is sufficiently close to reality, permitted the relative position range (in % of the thickness) to be determined where the fraction of active phase stripped off by attrition was situated.

Because of the roughness of the spheres defining the support, a portion of the dust collected was nothing other than the constituent material of these spheres, namely, clay. This proportion of clay in the dust collected increased in significance as the length of attrition increased. It was therefore more significant in the later collections. A sample of these inert spheres, of clay sintered at high temperature, was therefore ground in order to determine the quantity of potassium contained in the clay of the support. On the other hand, the dust collected was analyzed by X-ray fluorescence to determine, by the response of the element silicon relative to mechanically standardized mixtures, the proportion of clay which they contained. All parameters considered, it was thus possible to determine by difference the quantity of potassium and of phosphorus contained in each collection.

The values obtained for the catalyst of Example 1 are reported in Table I below, compared with the theoretical value expected if the distribution of the dopants was perfectly homogeneous:

TABLE I

| Position (% of the thickness) | Crude content K ppm | Crude content P ppm | Clay % by weight | Contents in the fraction of active phase K ppm | Contents in the fraction of active phase P ppm | Expected Theoretical content K ppm | Expected Theoretical content P ppm |
|---|---|---|---|---|---|---|---|
| Exterior 100 to 26 | 480 | 270 | 2 | 460 | 263 | 392 | 310 |
| 26 to 16 | 415 | 260 | 1 | 404 | 256 | 392 | 310 |
| 16 to 11 | 450 | 245 | 4 | 401 | 227 | 392 | 310 |
| Interior 11 to 6.5 | 770 | 225 | 8 | 677 | 191 | 392 | 310 |
| Central clay | 1110 | 410 | 100 | | | | |

It will be seen that the contents of dopants were overall very close to the value expected if the distribution was really homogeneous. (The persistent difference for phosphorus is likely explained by a systematic error of measurement, or a slight loss in the clay of the support). Overall, the rates of incorporation were controllable and close to 100%.

As regards the distribution in the thickness of the active phase, the contents appear constant at ±15% for potassium if the value for the innermost layer was excepted, this being in all likelihood the most affected by the presence of clay. For phosphorus, there appeared to be a variation of ±30%, apparently more systematic as a function of the depth of the layer.

By way of comparison, the values measured on the catalyst prepared according to Comparative Example A are reported in Table II below:

TABLE II

| Position (% of the thickness) | Crude content K ppm | Crude content P ppm | Clay % by weight | Contents in the fraction of active phase K ppm | Contents in the fraction of active phase P ppm | Expected Theoretical content K ppm | Expected Theoretical content P ppm |
|---|---|---|---|---|---|---|---|
| Exterior 100 to 28 | 2260 | 920 | 2 | 2241 | 913 | 607 | 481 |
| 28 to 19 | 2315 | 890 | 1 | 2308 | 887 | 607 | 481 |
| 19 to 13 | 2190 | 890 | 1 | 2176 | 885 | 607 | 481 |
| Interior 13 to 5.7 | 2165 | 880 | 11 | 2038 | 833 | 607 | 481 |
| Central clay | 1110 | 410 | 100 | | | | |

It will be seen that the values are completely different from those which would be expected if the distribution of the dopants was homogeneous. The fraction of the batch of doped active phase examined proved too rich in dopants: about 4 times more for potassium and twice more in phosphorus. This is likely due to the inhomogeneity of distribution caused by the mixing. The rates of incorporation of the dopants do not appear to be controllable.

EXAMPLE 3

Influence of the Dopants on the Mechanical Resistance of the Finished Catalyst The mechanical resistance of the finished catalysts was determined by an attrition test as follows:

100 g of finished catalyst were introduced into a Plexiglass ® drum of exterior diameter 200 mm and of breadth 40 mm fixed on the horizontal shaft of a motor revolving at 10 revolutions per minute. In the interior of the drum were fixed, at regular intervals, 6 planar Plexiglass ® blades 45 mm long and 40 mm wide, inclined at 40° with respect to the diameter traversing their fixing base.

The direction of rotation of the drum was such that, if the vector of the tangential velocity of the drum was represented by a point of fixation of any one of the blades, this would define an angle of 50° with the blade.

The drum was rotated for 5 minutes, then the spheres were removed from the drum and weighed after sieving to separate the fines. The mass thus determined is $m_5$. Dust was removed from the apparatus, then the spheres were reintroduced. A new weighing was carried out at the end of 10 minutes, providing a mass $m_{15}$.

The rate of attrition is defined as the proportion of active phase removed by the attrition device. It is calculated with respect to the amount T of active phase in the following manner:

After 5 minutes, the rate of attrition, in %, had the value $(100 - m_5) \times 100/T$.

After a total of 15 minutes of attrition, the rate had the value $(100 - m_{15}) \times 100/T$.

The measurements of attrition carried out on different batches of 169 kg of catalyst prepared according to the procedure of Example 1 according to the invention are reported in the following Table III, in comparison with those carried out on a catalyst prepared according to the conditions of Example B, and thus not doped:

TABLE III

| Example | Dopants | Content T (%) | Rate of attrition at 5 mn (%) | Rate of attrition at 15 mn (%) |
|---|---|---|---|---|
| 1-batch 1 | $KO_{0.028}PO_{0.028}$ | 26 | 0.00 | 0.38 |
| 1-batch 2 | $KO_{0.028}PO_{0.028}$ | 26 | 0.00 | 0.08 |
| 1-batch 3 | $KO_{0.028}PO_{0.028}$ | 26 | 0.23 | 0.31 |
| B | KO PO | 26 | 0.23 | 0.46 |

As a catalyst is considered as solid from the instant where the result of these measurements is less than 1% per minute of attrition, it will be seen that the catalysts prepared according to the process of the invention were very resistant. In addition, the apparent dispersion of the results in the different batches did not have any important physical significance, since the values were all very small.

It will be seen that, contrary to that which would have been expected, the presence of dopants in the coating solution did not modify the mechanical resistance of the catalyst in a significant manner.

EXAMPLE 4

Activity of the Formulation Prepared According to the Invention

A sample of 100 ml of catalyst prepared according to Example 1 was tested in the oxidation reaction of propylene to acrolein. The reactor used had a 21 mm internal diameter and a height of 50 cm.

The reaction mixture introduced into the reactor heated by a sand bath contained, in percent by volume, 7% of propylene, 57% of air and 36% of water vapor. The supply of propylene was adjusted to provide a charge of about 250 g of propylene per hour and per liter of catalyst. The outlet pressure of the reactor was adjusted to 1.8 bar absolute.

The effluents from the reactor comprised a gaseous mixture of nitrogen, oxygen, water vapor, propylene, acrolein, acrylic acid, acetic acid, acetaldehyde, carbon monoxide and dioxide and other impurities in minor amounts. Gas phase chromatographs permitted the proportions of each of these products to be determined and thus the catalytic performances to be calculated, namely:

The rate of conversion, designated $X_g$ $$X_g = \frac{\text{Number of moles of propylene consumed}}{\text{Number of moles of propylene introduced}} \times 100$$

The selectivity for product i, designated $S_i$ $$S_i = \frac{\text{Number of moles of product } i \text{ formed}}{\text{Number of moles of propylene converted}} \times 100$$

and $R_i$ which is the yield of product i. The yield is the product of the conversion $X_g$ multiplied by the selectivity for product i: $R_i = X_g \times S_i$ The results obtained on the catalyst prepared according to Example 1 are reported in the following Table IV:

TABLE IV

| Dopants | Contents (%) | Temperature of bath °C. | $X_g$ (%) | $S_{acrolein}$ (%) | $S_{acrylic}$ (%) | $S_{CO-CO_2}$ (%) | $R_{acrolein}$ (%) |
|---|---|---|---|---|---|---|---|
| $KO_{0.028}PO_{0.028}$ | 26 | 357 | 95.9 | 78.6 | 12.6 | 4.3 | 75.4 |

It will be seen that the catalyst thus prepared according to the process of the invention permitted good catalytic performances to be obtained, namely, a high yield of acrolein at a high value of conversion of propylene.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of coated catalyst particulates, the coating layer of which consists essentially of a catalytically active phase including a catalytically effective amount of bismuth and iron molybdate and dopant amounts of phosphorus and potassium, comprising providing a calcined and ground catalytically active intermediate composition devoid of phosphorus and potassium values, coating said intermediate composition onto a particulate support substrate comprising rough-surfaced inert and solid spheres. also coating phosphorus and potassium values onto said particulate support substrate, and then calcining the support particulates thus coated.

2. The process as defined by claim 1, comprising coating said particulate support substrate with an aqueous solution of at least one potassium compound and at least one phosphorus compound.

3. The process as defined by claim 2, the solubility in water of the at least one phosphorus compound and of the at least one potassium compound, measured at 25° C., being greater than 10 g/l.

4. The process as defined by claim 2, the pH of said aqueous solution ranging from 3 to 11.

5. The process as defined by claim 2, said aqueous solution comprising an adhesive agent.

6. The process as defined by claim 2, said at least one potassium compound comprising potash.

7. The process as defined by claim 2, said at least one phosphorus compound comprising phosphoric acid or an inorganic or organic phosphate.

8. The process as defined by claim 2, said at least one phosphorus compound and said at least one potassium compound comprising potassium mono- or dihydrogen phosphate.

9. The process as defined by claim 2, said aqueous solution comprising within ±5% of the amount of potassium and phosphorus theoretically required to provide the desired stoichiometry in the final product catalyst.

10. The process as defined by claim 1, comprising calcining the coated support particulates at a temperature ranging from 450° to 500° C.

11. A process for the preparation of catalyst particulates having a coating layer comprising a catalytically active phase including a catalytically effective amount of bismuth and iron molybdate and dopant amounts of phosphorus and potassium, comprising providing a calcined and ground undoped catalytically active intermediate composition devoid of phosphorus and potassium values, coating said undoped intermediate composition onto a particulate support substrate comprising rough-surfaced inert and solid spheres, coating dopant amounts of phosphorous and potassium values onto said particulate support substrate, and then calcining the support particulates thus coated.

12. The process as defined by claim 11, comprising coating said particulate support substrate with an aqueous solution of at least one potassium compound and at least one phosphorous compound.

13. The process as defined by claim 12, the solubility in water of the at least one phosphorous compound and of the at least one potassium compound, measured at 25° C., being greater than 10 g/l.

14. The process as defined by claim 12, the pH of said aqueous solution ranging from 3 to 11.

15. The process as defined by claim 12, said aqueous solution comprising an adhesive agent.

16. The process as defined by claim 12, further comprising preparing said undoped catalytically active intermediate composition by precipitating a molybdenum, bismuth and iron containing precipitate from an aqueous solution, forming a calcined product by calcining the precipitate and then grinding the calcined product.

17. The process as defined by claim 12, said at least one phosphorous compound comprising potash, phosphoric acid or an inorganic or organic phosphate.

18. The process as defined by claim 12, said at least one phosphorous compound and said at least one potassium compound comprising potassium mono- or dihydrogen phosphate.

19. The process as defined by claim 2, said aqueous solution comprising within ±5% of the amount of potassium and phosphorous theoretically required to provide the desired stoichiometry in the final product catalyst.

20. The process as defined by claim 11, comprising calcining the coated support particulates at a temperature ranging from 450° to 500° C.

* * * * *